(12) United States Patent
Santamaria-Pang et al.

(10) Patent No.: US 8,831,327 B2
(45) Date of Patent: Sep. 9, 2014

(54) SYSTEMS AND METHODS FOR TISSUE CLASSIFICATION USING ATTRIBUTES OF A BIOMARKER ENHANCED TISSUE NETWORK (BETN)

(75) Inventors: Alberto Santamaria-Pang, Schenectady, NY (US); Daniel Eli Margolis, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 467 days.

(21) Appl. No.: 13/221,091

(22) Filed: Aug. 30, 2011

(65) Prior Publication Data

US 2013/0051650 A1 Feb. 28, 2013

(51) Int. Cl.
*G06K 9/00* (2006.01)
*G06F 19/24* (2011.01)

(52) U.S. Cl.
CPC ...................................... *G06F 19/24* (2013.01)
USPC .......................................................... 382/133

(58) Field of Classification Search
None
See application file for complete search history.

(56) References Cited

U.S. PATENT DOCUMENTS

| | | | |
|---|---|---|---|
| 2005/0262031 A1 | 11/2005 | Saidi et al. | |
| 2009/0161928 A1* | 6/2009 | Khamene et al. | 382/128 |
| 2009/0298703 A1* | 12/2009 | Gough et al. | 506/8 |
| 2010/0178653 A1 | 7/2010 | Aharonov et al. | |
| 2011/0122138 A1* | 5/2011 | Schmidt et al. | 345/440 |
| 2011/0295782 A1* | 12/2011 | Stojadinovic et al. | 706/12 |
| 2011/0312530 A1* | 12/2011 | Aharonov et al. | 506/9 |
| 2013/0051650 A1* | 2/2013 | Santamaria-Pang et al. | 382/133 |
| 2013/0259839 A1* | 10/2013 | Aharonov et al. | 424/93.7 |

FOREIGN PATENT DOCUMENTS

| | | |
|---|---|---|
| WO | 9534050 A1 | 12/1995 |
| WO | 2010046625 A1 | 4/2010 |
| WO | 2010073248 A2 | 7/2010 |
| WO | 2011005893 A2 | 1/2011 |
| WO | 2013030175 A2 | 3/2013 |

OTHER PUBLICATIONS

Margolis, Daniel, Alberto Santamaria-Pang, and Jens Rittscher. "Tissue segmentation and classification using graph-based unsupervised clustering." Biomedical Imaging (ISBI), 2012 9th IEEE International Symposium on. IEEE, 2012.*
Wang et al., "A Neural Network-Based Biomarker Association Information extraction approach for cancer classification", Journal of Biomedical Informatics, vol. 42, Issue 4, pp. 654-666, Aug. 2009.
Ali et al., "Boosted Segmentation Algorithm for Detecting Nuclei in Fluorescence Microscopy Images", U.S. Appl. No. 12/757,668, filed Apr. 9, 2010; 16Pages.
WO search report attached; Application No. EP 2012/066648, Filed on Aug. 28, 2012.

* cited by examiner

*Primary Examiner* — Tahmina Ansari
(74) *Attorney, Agent, or Firm* — Seema S. Katragadda (57) ABSTRACT

Methods and systems for tissue classification of a tissue sample are provided. The methods and systems transform the tissue image data to a biomarker enhanced tissue network (BETN) such that an individual cell or a sub-cellular structure in the tissue image data corresponds to a node in the BETN, define a feature vector based on a feature set representative of a tissue type of interest, cluster nodes of the BETN based on a similarity criterion of one or features of the feature vector, and classify the nodes in the tissue image data based on the grouping of the nodes of the BETN.

25 Claims, 7 Drawing Sheets

SYSTEMS AND METHODS FOR TISSUE CLASSIFICATION USING ATTRIBUTES OF A BIOMARKER ENHANCED TISSUE NETWORK (BETN)

BACKGROUND

Embodiments of the invention relate to tissue images and more specifically to classification of objects in the tissue images to extract content from the images.

Tissue classification at a cellular level is desirable for medical diagnostic or prognostic purposes. Typically, for diagnostic or prognostic purposes pathologists acquire tissue samples through biopsy, view them with microscopes at high resolutions, and manually analyze the images. Pathologists rely on training and experience to determine tissue types or obtain diagnostic or prognostic information from the tissue images. Depending on the type of information desired by a pathologist, different biomarker stains are used to view a tissue sample. Each stain provides a distinctive view of the tissue and contains distinct information about a portion of the tissue. Differences in the uptake of the biomarker stains by different types of cells and cell parts are used for differentiating and quantifying cells in the tissue. While the methods for tissue classification performed by the user (i.e., the pathologist) on images requiring analysis may be effective in classifying basic tissue types, these methods suffer from high inefficiency and user variability. Also, the manual method is unable to utilize the complex information that can be gained from viewing the tissue across multiple stains, and may lack reproducibility.

Digitization of images is used to reduce some of the inefficiency problems; however, despite the digitization of the images, the methods depend primarily on the ability of the user to produce fast, accurate, complex results.

By combining the information gathered using different stains, a more comprehensive picture of the tissue sample may be obtained. With image registration, images of different staining of the same tissue may be aligned to form a multiplex image. Using all of the distinctive data content from each stain, image segmentation may be performed at the intercellular and intracellular levels. The result of this process may provide a dataset containing quantitative information on the size, shape, and staining level of each cell, cell membrane, cell nucleus, and cell cytoplasm, for every stain. However, the image segmentation process may occasionally fail or misclassify cells, or may not be able to handle artifacts or out of focus images.

Given sufficient labeled training data, traditional classification techniques may be capable of developing classifiers that may be patient, gland, and tissue specific. With a proper annotation tool and real time classification, these classification techniques along with machine learning techniques may perform specific tasks in the clinical setting. However, these classification techniques are unable to manage the wide variety of gland configurations and tissue types.

Therefore, it is desirable to have an enhanced method of tissue segmentation and classification that is automated and more reliable, to enhance diagnostic and prognostic information and subsequent treatment and to reduce costs and errors in tissue classifications

BRIEF DESCRIPTION

In one example, a method for tissue classification is provided. The method comprises acquiring tissue image data from a tissue sample wherein the technical effect is to transform the tissue image data to a biomarker enhanced tissue network (BETN) such that an individual cell or a sub-cellular structure in the tissue image data corresponds to a node in the BETN, define a feature vector based on a feature set representative of a tissue type of interest, cluster nodes of the BETN based on a similarity criterion of one or more features of the feature vector, and classify the nodes in the tissue image data based on the grouping of the nodes of the BETN.

In another example, a method for tissue classification of a tissue sample is provided, wherein the tissue is treated to reveal levels of protein expression of one or more biomarkers, and wherein the technical effect is to acquire one or more tissue images of the tissue sample, determine a probabilistic network based on the tissue images such that each node in the probabilistic network corresponds to a cell in the tissue images, determine a BETN by combining the levels of protein expression of the one or more biomarkers, determine a feature vector based on a feature set of the BETN such that the feature vector is representative of a tissue type of interest, determine nodes that satisfy a similarity criterion based on the feature vector, classify the nodes using an algorithm, and overlay classification data of the nodes on corresponding cells of the tissue images.

An embodiment of an image analysis system for analyzing a tissue sample is provided. The system comprises an imaging device configured to image a tissue sample, and a processor programmed to determine a BETN based on the tissue image data such that an individual cell in the tissue image data corresponds to a node in the BETN, define a feature vector based on a feature set representative of a tissue type of interest, cluster nodes of the BETN based on a similarity criterion of the feature set of the nodes, and classify cells in the tissue image data based on the grouping of nodes of the BETN.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The systems and methods for classifying tissues may be configured for automated and intelligent cellular and sub-cellular classification of the tissue sample. Data obtained from the tissue images may comprise spatial, morphological, and biomarker or stain related data. The spatial information may comprise information about neighborhood cells of the individual cells that comprise the tissue image. For example, the spatial information may include information about the type and number of neighborhood cells of one or more individual cells. The morphological information may include information about different types of cells (e.g. stroma or epithelial cells) that may be present in the tissue sample.

The tissue images may be digitally segmented at the cellular and sub-cellular levels. That is, the tissues may be segmented into individual cell units. The cell units may be further segmented into sub-cellular compartments, such as but not limited to, nucleus, membrane and cytoplasm. The image data may be obtained from one or more compartments of each cell. The features, such as levels of protein expression of biomarkers, may be obtained from the different compartments of the individual cells. A level of protein expression, for example, is an indicator of the strength of the signal from the label associated with a probe for that biomarker for all the cells associated with that compartment. Thus, a sum may be taken across all the cells associated with a given compartment of a cell for evaluating the signal strength associated with each biomarker for the given compartment of the cell.

In certain examples, methods for tissue classification may comprise acquiring tissue image data for a tissue sample. The tissue image data may comprise data from one or more tissue images. The tissue images may comprise a field of view of a tissue sample treated to reveal protein expression data for one or more biomarkers. The tissue image data may be transformed to a biomarker enhanced tissue network (BETN) such that an individual cell or a sub-cellular structure in the tissue image data corresponds to a node in the BETN. A feature vector based on a feature set representative of a tissue type of interest may be defined. Nodes of the BETN may be clustered or grouped based on a similarity criterion of one or more features of the feature vector. The grouped nodes that comprise desirable values for threshold settings may be segmented in the BETN. The classification data of the nodes may be mapped on corresponding cells of the tissue image data. The tissue image data comprising the biomarker stain data and classification data may be displayed.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, the term "betweenness" refers to an extent to which a node lies between other nodes in the network.

As used herein, the term "cluster size" refers to a number of nodes to or with which a particular node is connected or associated. The particular node may be connected directly or indirectly (via other nodes) to the number of nodes represented by the cluster size.

As used herein, the term "clustering coefficient" refers to a measure of the likelihood that two associates of a node are associates themselves.

As used herein, the terms "degrees" or "degrees number" refer to a number of nodes that a node is directly connected or linked to.

As used herein, the term "centrality" is an indication of how well a particular node connects the network. For example, betweenness and degrees are measures of centrality.

As used herein, the term "flow" refers to a degree by which a particular node contributes to sum of maximum flow between all pairs of nodes.

Methods for tissue classification may be performed on a single tissue sample or multiple tissue samples. The samples may be drawn from a single subject or multiple subjects. In one embodiment, the method for tissue classification may be used to classify different cell types in the tissue sample. In another embodiment, tissue samples from different locations in a particular subject may be classified. For example, stroma and epithelial tissues from the same organ of a subject may be segmented to determine differences between the two tissues. In another embodiment, samples of similar tissue types obtained from different subjects may be examined. For example, tumor tissue from two or more subjects treated with a particular drug under evaluation may be examined to determine the amount of effect of the treatment on the tissues of different subjects.

As a pre-process step, the tissue samples that are to be classified may be treated with labeled antibodies of antibody surrogates such as an epitope specific antibody fragments. The amount of each label that binds to the tissue may be measured. The antibodies or antibody surrogates are specific to a biomarker of interest and are typically directly or indirectly labeled with moieties that generate optical signals when interrogated with light of suitable wavelengths. In one embodiment, the tissue samples may be repeatedly treated, with each treatment involving antibodies or antibody surrogates specific to different biomarkers. In one embodiment, the signal generation from the immediately previous treatment may be neutralized by employing optical or chemical methods. The amount of each label bound to the biomarkers of interest by the antibodies or antibody surrogates may be measured by subjecting the tissue sample to the radiation of suitable wavelength, and imaging the response.

The slides may be stained with the labeled biomarker probes using for example, cytology procedures. In one embodiment, the initial staining of each slide may also involve the use of biomarkers for one or more of the cell compartments, such as but not limited to, a nucleus, cytoplasm and membrane. In one embodiment, biomarkers, that are not bleached when the labels attached to the biomarker probes are bleached, may be used. These procedures generally involve rendering the biomarkers in the slide tissue accessible to the labeled probes and incubating the labeled probes with the prepared slides for a desirable period of time. The slides may be simultaneously incubated with a number of labeled biomarker probes, each specific for a different biomarker. However, there may be a practical limit to the number of labeled probes that may be simultaneously incubated with a slide because each labeled probe is required to generate a signal which is fairly distinguishable from the signals generated by the other labeled probes. In one embodiment, a set of labeled probes specific to a set of biomarkers may be used to stain a slide, images of the stained slide may be acquired, and then optically or chemically the labels may be bleached to destroy their ability to generate signal. Another set of labeled probes specific to different biomarkers but with labeling moieties identical to those used in the prior staining step may then be used to stain the same slide. This approach may be used iteratively until images have been acquired of the same slide stained for all the biomarkers of interest.

The biomarkers may be conveniently selected in accordance with the biological phenomenon being examined. For instance, if a particular biological pathway is involved in the phenomenon under examination proteins involved in that pathway or the RNA encoding those proteins may be selected as the suitable biomarkers.

Any biomarkers suitable for a histological examination, to give an indication of the level of expression of the biomarker and are likely to vary in response to the biological condition or history of a selected tissue, may be used. The biomarkers may be DNA, RNA or protein based, or a combination thereof. Thus, a pattern of cells, within a tissue with a given gene having a certain level of occurrence different from the average level of occurrence among all the cells in that tissue, may be determined. Similarly, patterns of cells having a different level of RNA or protein expressions may be determined.

The level of expression of a biomarker of interest may be assessed by staining the slides of the tissue with a probe specific to the biomarker associated with a label that may generate a signal under appropriate conditions. Two useful probes are DNA probes with sequences complimentary to the DNA or RNA of interest and antibodies or antibody surrogates such as antibody fragments with epitope specific regions that specifically bind to the biomarker of interest that may be DNA, RNA or protein. In some examples, it is important that the probe is labeled in such a manner that the strength of the signal obtained from the label is representative of the amount of probe which has bound to its target.

One non-limiting example of a suitable probe, from the point of view of availability and well established characterization, is a monoclonal or polyclonal antibody specific for the biomarker of interest. There are commercially available antibodies specific to a wide variety of biomarkers. Mechanisms for associating many of these antibodies with labels are well established. In many cases the binding behavior of these antibodies is also well established.

The tissue image may be captured by the treatment and imaging of tissue samples. In certain embodiments, the treatment may comprise preparing slides of the tissue samples and staining the tissues using a suitable biomarker for staining the tissues to identify cell boundaries, cell compartment boundaries and levels of expression of the selected biomarkers. In certain embodiments, the biomarker stained tissue samples may be imaged for tissue classification. The imaging may comprise digital imaging of one or more desirable fields of view. The tissue images may comprise biomarker protein expressions. The imaging may comprise fluorescence imaging.

A representative number of fields of view may be selected for each tissue sample depending upon the nature of the sample. For instance, if a slide is made of a single tissue sample, numerous fields of viewer may be available, while if the target of examination is a tissue microarray (TMA) a more limited number of fields of view may be practical.

In certain embodiments, the images of each field of view are acquired with a digital camera coupled with an appropriate microscope and appropriate quality control routines. In one example, the microscope may be designed to capture fluorescent images and be equipped with appropriate filters. In this example, the microscope may be controlled by software that assures proper focus and correction for auto-fluorescence. An example routine for auto-fluorescence may comprise acquiring a reference image using the filter appropriate for a given fluorescent label but with no such label active in the image and then using this reference image to subtract the auto-fluorescence at that wavelength window from an image in which the fluorescent label is active.

In certain embodiments, a plurality of biomarker stains may be used to view a tissue sample. For example, the plurality of biomarkers may be used such that each stain may give a distinctive view of the tissue that contains distinct information about a portion of the overall tissue. The images of different stains may be acquired to provide a relatively comprehensive picture of the tissue. The combined images, referred to as a multiplex image, may be used for tissue classification.

In embodiments where the approach of iteratively staining and bleaching a slide is used, to obtain information on numerous biomarkers, it may be desirable to provide a mechanism for the images of each field of view from each round to be properly aligned with the images of the same field of view from previous rounds. In these embodiments, more than one image is taken of a given field of view, hence, it is desirable that the successive images, commonly collectively referred to as a stack, be kept in registry. In one example, the field of view of each of the image in the stack is aligned such that the same feature or features are present in each image of a field of view. For example, the feature may be a pattern of cell nuclei as revealed by an appropriate stain. One of the images of the stack may be taken as a reference, and appropriate transformations may be applied to the other images in that stack to bring them into registry. In one example, the first image taken may be used as the reference.

In certain embodiments, imaging of the tissues may be followed by transforming the tissue image to a network, where each node represents a cell. In these embodiments, a plurality of nodes constitutes a network, with each node corresponding to a cell in the tissue image. After the classification of the tissue, each node is connected to every other node of the same cluster or group. Each node of a group may have multiple connection lines originating from that node and reaching out to other nodes in that group of the network. Hence, the connection lines or links may originate, intersect or branch from a node.

In one embodiment, the network may be a probabilistic network, such as but not limited to, a Bayesian network. In the network, each cell is treated as a node and each node serves as a carrier of information for the corresponding cell, which the node represents. The node may contain information on one or more of a nuclei, cytoplasm, and membrane of the cell that it represents.

In certain embodiments, a biomarker enhanced tissue network (BETN) may be formed by combining the network model with the staining data. The staining data may be provided for each node of the network. A plurality of biomarkers may be used to produce spatial and protein patterns of the cells. The BETN network model may be configured to classify multiple tissue types. The staining information may be displayed by assigning different colors to nodes based on the level of staining of the nodes by a particular biomarker. In embodiments where a plurality of tissues is to be classified in a tissue sample, the BETN may be normalized for each individual tissues. The measurement values may be normalized using any mathematical statistical techniques. In one example, the mean and standard deviation of all the measurements associated with a given biomarker in a given study may be obtained and this mean value may be subtracted from each measurement value. The resultant difference may be divided by the standard deviation to obtain normalized or standardized value. This normalized or standardized value may be generated as part of the numerical interrogation. In one example, the normalized or standardized value may be stored in the database.

The BETN may use attributes of the network in combination with the features of the tissues and cells for classifying tissues based on features of cell, cytoplasm, membrane, and nucleus for a particular biomarker stain. Non-limiting examples of the attributes of the network may comprise betweenness, degrees, flow, clustering coefficient, and cluster size. The attributes of the network may be assigned threshold settings to enable classification of the different tissue types in the tissue sample. The different stain types may result in different networks based on the properties of that stain and provide specific information that may be used to quantify tissues for classification. The BETN enables a single model to be used for classification of different tissue types and gland structures by adjusting the threshold settings. In one example, the threshold settings may be adjusted to modify sensitivity of classification. A higher threshold setting may cause node connections to be more likely, thereby resulting in a greater number of nodes being connected.

In certain embodiments, features of cells that are specific to a particular type of cell, and/or features that are network wide may be used to group the nodes in the tissue sample. These features may also be used to develop features describing the tissue architecture. In one example, the BETN network may be adapted to use with tissues with different gland structures, easily separable glands, small cells, large cells, and different tissue types (e.g., lung, colon, prostate, etc.). The model is configured to determine quantitative differences within glands, tissues, and between glands and tissues. In addition to classification, the methods may also be used for feature construction using the attributes of the network.

The tissue features may be used for differentiating tissue types and determining tissue architectures. For example, the measurement of a level of expression of multiple biomarkers in individual cells or in the sub-cellular compartments of the individual cells may be used as a feature. In one embodiment, information may be derived from the different compartments of the cells, such as but not limited to, nucleus, cytoplasm and membrane of the cells. Non-limiting examples of features may include the area of a cell, area of a nucleus of a cell, area of a membrane of a cell, area of the cytoplasm in a cell, and quantification values of protein (biomarker) expressions of the cells. In one example, a feature set may include, but is not limited to, mean protein expression level, standard deviation protein expression level, maximum protein expression level, and minimum protein expression level of the membrane and/or the cytoplasm of the cell. Some or all of the selected features may be used for tissue classification. Additional cell features may comprise cell morphology and location of the cell in the tissue architecture such as proximity to a particular feature like a blood vessel. In certain embodiments, one or more features representative of the tissue type may be selected from the network or the BETN. For example, the biomarkers may be used to generate features that may enable encoding of spatial and protein expression patterns of the cells.

A preliminary feature set may be selected, for example, from the probabilistic network or the BETN. In one embodiment, the preliminary feature set may be selected based on a priori knowledge. A preliminary feature vector may be constructed from the preliminary feature set. A machine learning technique may be used to obtain baseline results using the preliminary feature vector for tissue classification. The machine learning techniques may require a supervised learning technique. That is, the machine learning techniques may require labeled or "known" data to create the decision boundary. In certain embodiments, the machine learning technique may be used for preliminary classification of the tissue, and optionally, based on this preliminary classification, the preliminary feature set may be revised. The preliminary feature set may be revised manually by the user or automatically by the system. In one example, the revised feature set may be a subset of the preliminary feature set. In certain other embodiments, the preliminary feature set derived from the probabilistic network or the BETN may be used as a feature set for tissue classification without down selecting the feature set. Based on the selected feature set, a feature vector may be constructed. The feature vector may be an n-dimensional vector that is representative of a tissue type. The vector space associated with the vectors of the feature vector may be referred to as a feature space.

In one example, a preliminary feature set of suitable size may be generated. The feature set may be used to form a feature vector. In this embodiment, a support vector machine (SVM) may be used, for example, to provide the baseline results for tissue classification. The SVM model may be used to determine parameters and a decision boundary. In the SVM, the input data may be kernelized (transformed) into feature space (Hilbert space) where distance between nodes represents the similarity between the nodes (cells). The SVM may be used to determine the decision boundary that has the maximum possible minimum distance to vectors, in the form of a hyperplane. The SVM process may provide non-linear decision boundaries in normal input; these non-linear decision boundaries may be linear boundaries in the feature space. In one embodiment, an algorithm may be developed, using an SVM as a fitness function, to determine which features and combination of features are desirable for tissue classification.

In one example, a plurality of SVM models may be produced on smaller sub-sets of nodes. The plurality of SVM models produced on smaller subsets may be then combined to use collective intelligence to determine a subset of features (feature set) from the preliminary feature set that may be informative for classifying the data.

In certain embodiments, for each feature in the revised feature set, a mean for the tissue sample may be determined. The terms "feature set" and "revised feature set" are used interchangeably throughout this description. The feature vector may be used to arrive at a similarity criterion to determine whether a link may occur between two nodes of a given pair of nodes. The feature vector may be developed using different stains, distances between nodes, and other useful information, such as spatial and morphological information, in various combinations to form different networks. In one embodiment, a mean of one or more features may be used as a baseline to determine whether a connection should be formed between a given pair of nodes. When determining whether a connection should be made between a given pair of cells, the averages for each feature may be compared to the baseline mean for both the nodes of the pair. The average of all such comparisons may be used to modify the distance metric of the nodes. The spatial distance between the two nodes may be divided by this modifier. In one example, the above average stain levels produce a shorter distance and below average stain levels produce a larger distance.

In certain embodiments, the pre-classification step may be performed using machine learning techniques which operate under supervision provided by a known classification for each of a number of training examples. The supervised machine learning facilitates identification of features that may be informative for classifying the data. The supervised machine learning is designed to learn (to approximate the behavior of) a function that maps the feature vector $(F_1, F_2, \ldots F_N)$ into one of several classes by considering a plurality of input-output examples (training data) of the function. The training data may comprise pairs of input objects (vectors) from clinical data, and the pathological proven class.

In certain embodiments, classification algorithms may be used to classify the tissues. The classification of the tissues may comprise classification of the nodes corresponding to the cells of the tissues. The cell specific and network based features may be used for classification algorithms. The characteristics of the network facilitate determination of the structure of the network. For example, the network characteristics may be used to differentiate glands, determine outer cells of a gland, shape and properties of the gland, density of a particular area, and the like.

The classifier may be an algorithm representing connectivity in the BETN. The classifier may be one or more attributes of the BETN network that are representative of the connectivity in the network and may be expressed as an algorithm. Non-limiting examples of the neighborhood based features of the BETN network may comprise robustness, or classifier algorithms for finding frequent subgraphs. Classifier algorithms may include, but are not limited to, betweenness, cluster size, clustering coefficient, degrees, centrality, flow, or combinations thereof.

In certain embodiments, the neighborhood based features may, at least in part, be derived, or classification may be performed, from the use of Center-Piece Subgraphs (CePS), Graph-based Hierarchical Conceptual Clustering, SUBstructure Discovery Using Examples (SUBDUE), Apriori-based Algorithm, GrAph, Sequences, and Tree extraction (GASTON), Graph-based induction, SPanning tree based maximal graph mINing (SPIN), Graph-based Substructure Pattern Mining (gSpan), Fast Frequent Subgraph Mining (FFSM), Leap Search, or combinations thereof. In one embodiment, features are derived, or classification may be performed, by converting graphs into trees or forming trees directly from the data for analysis with methods including CMTreeMiner.

A suitable algorithm for connectivity for the BETN may be used to perform classification tasks on a number of tissue types and derive significant features about the overall tissue. The methods may adjust sensitivity depending on a given application. The methods may be configured in various ways to provide infinite features for differentiating tissue and discovering knowledge.

In certain embodiments, supervised or partially supervised learning may be used in an iterative manner with the BETN model. In one embodiment, a group of cells that have a threshold level of expression of certain proteins may be identified and then one or more subgroups of that group may be created using supervised grouping based on a plurality of biomarkers that may or may not include the original criteria proteins. In another embodiment, subgroups of a group of cells may be created by unsupervised grouping using partially or fully supervised grouping. In yet another instance a group might be created by unsupervised grouping that is of particular interest and then a further application of the grouping routine may be used to identify other groups of cells that are similar to this group.

In certain embodiments, cells of interest may be selected in the tissue image, and this selection may be used to highlight similar cells in an image. In these embodiments, an annotation interface may be provided. The annotation tool or interface may overlay one or more markers for the cells onto the original tissue image. In one embodiment, the annotation tool may be used to label the different tissue types. The labels of the different tissue types may be provided by the user.

In certain embodiments, boosting techniques may be applied to the BETN during classification of the tissues. In these embodiments, each time a cell or a set of cells is selected, the model may update the BETN and apply the change to the tissue image as the selection process continues. The boosting may make the tissue classification process interactive, in which the cells of interest may be chosen, and similar cells may be subsequently highlighted in the tissue image.

In certain embodiments, the systems and methods may form a part of an automated platform for analysis of multiplexing imaging. The methods and algorithms may be used as a clinical tool to facilitate personalized prognosis, diagnosis and therapies of patients, such as skin cancer patients.

Figure 1:
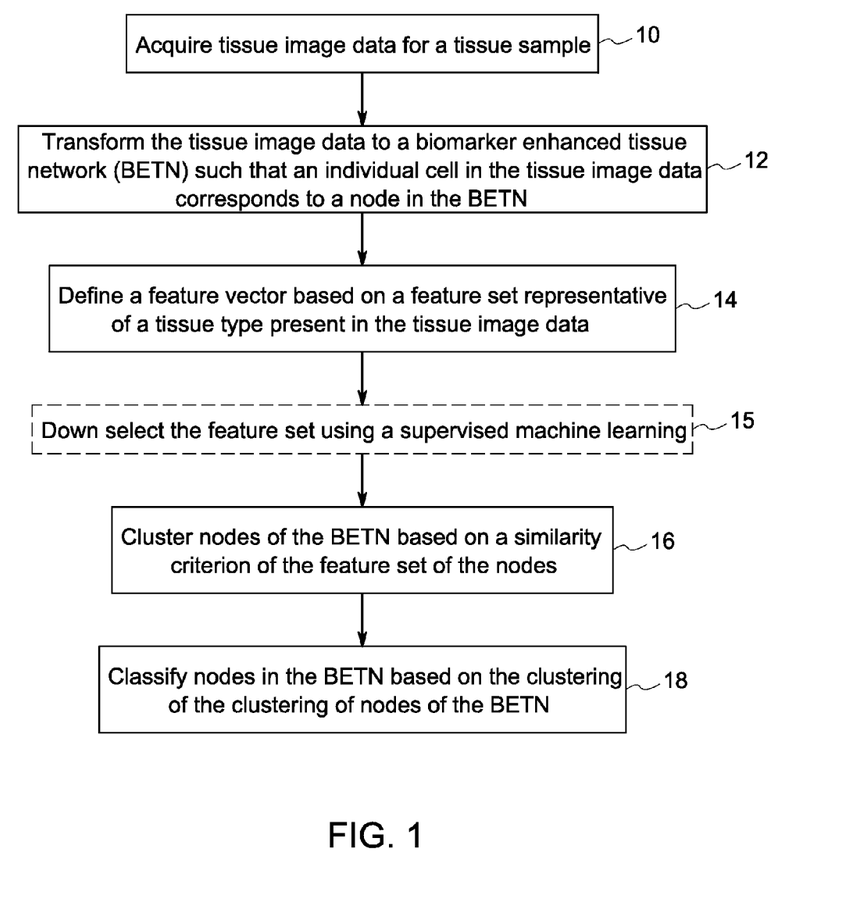
FIG. 1 is a flowchart of an example method for tissue classification using individual cells as nodes in a biomarker enhanced tissue network (BETN) of a tissue sample.

FIG. 1 is an example of a method for enhanced tissue classification. The method may comprise computer executable instructions. Generally, computer executable instructions may include routines, programs, objects, components, data structures, procedures, modules, functions, and the like that perform particular functions or implement particular abstract data types. In some embodiments, the computer executable instructions may be located in computer storage media, such as a memory, local to the system or in operative association with the processor. In other embodiments, the computer executable instructions may be located in computer storage media, such as memory storage devices, that are removed from the system. Moreover, the method of enhanced tissue classification may comprise a sequence of operations that may be implemented in hardware, software, or combinations thereof.

At step 10, tissue image data that may be representative of tissue characteristics of interest may be acquired. At step 12, based on the tissue image data a stain modified network model, also referred to as the BETN in the present application may be determined such that a cell in the tissue image data corresponds to a node in the BETN. In one embodiment, the BETN model uses features for cell, cytoplasm, membrane, and nucleus for a particular stain. In embodiments where two or more tissue samples are used, the BETN models of the individual tissue samples may be normalized for each individual tissue sample.

At step 14, a feature vector may be defined based on a feature set representative of a tissue type present in the tissue image. For each feature, a baseline mean for the tissue sample may be determined.

At step 15, supervised machine learning may be employed to down select the feature set. In one embodiment, for each feature a baseline mean may be used for similarity criterion. In this embodiment, an average for one or more features of the pair of nodes may be compared to the baseline mean of those features for that tissue. The average of all the comparison may be used to modify the distance metric. The spatial distance between any two nodes may be divided by this modifier. In one example, the above average stain levels may produce a shorter distance and below average levels may produce a larger distance. This is then used against the same threshold as the original model to determine links in the network. In one example, the similarity criterion may be used to form links or connections between two given nodes.

At step 16, nodes of the BETN may be grouped based on the similarity criterion of the features of the feature set. At step 18, tissues in the image data may be segmented or classified based on the grouping of the nodes of the BETN.

Advantageously, the use of classifiers enables the methods in combination with two or more stains may be used for classification of different tissue types and gland structures with only adjustments needed for the threshold settings or the values of the classifiers. Different stain types may result in different networks based on the properties of that stain and provide specific information that may be used to quantify tissues for classification. The threshold settings may be selected based on the tissue and gland type in the tissue sample. In one example, a higher threshold may cause connections to be more likely and resulting in more cells being connected.

Figure 2:
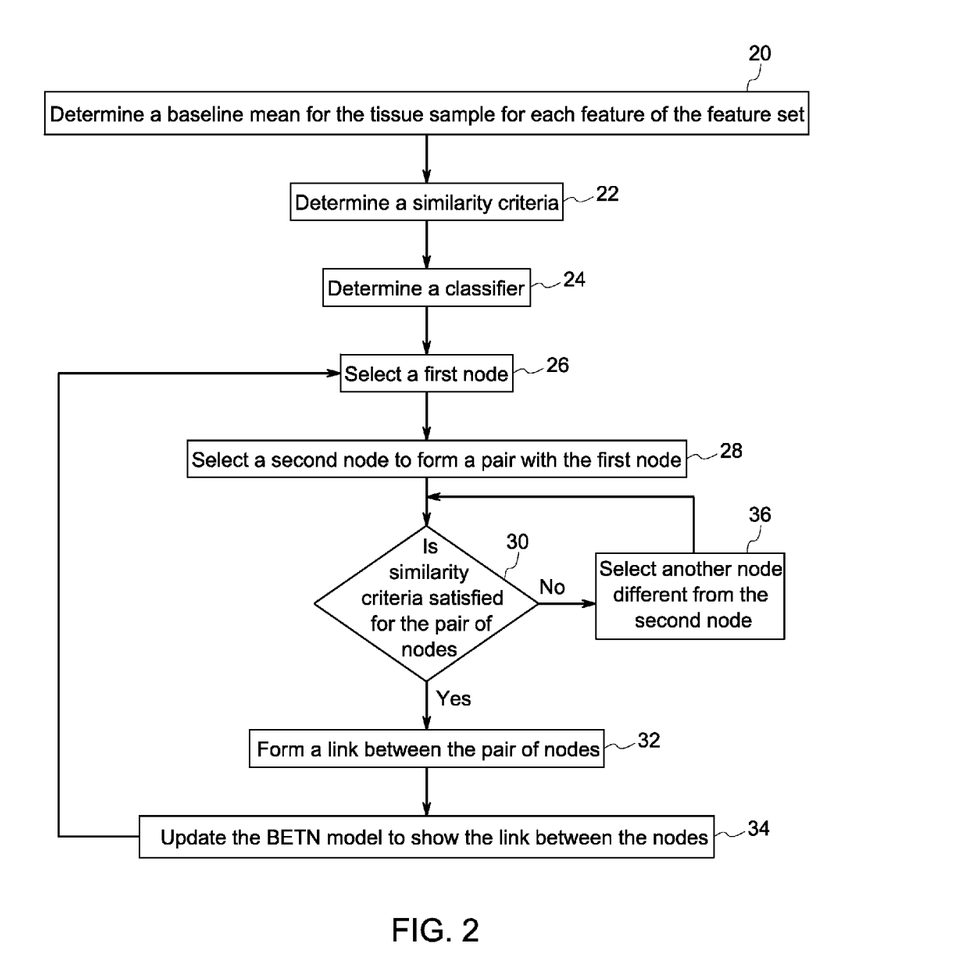
FIG. 2 is a flow chart of an example method for determining a link formation between a given pair of nodes using similarity criterion.

FIG. 2 illustrates an example procedure for determining a link formation between a given pair of nodes using similarity criterion. At step 20, a baseline mean of the tissue sample is determined. In one embodiment, the baseline mean may be determined for one or more features of the feature set. In another embodiment, the baseline mean may be decided individually for each feature of the feature set. In one embodiment, the similarity criterion may comprise comparing a baseline mean of the tissue sample with the average mean of the features of the pair of nodes. Although described with respect to the baseline mean, the similarity criterion may not be limited to the baseline mean, but may comprise other mathematical functions, such as but not limited to baseline variance or standard deviation, non-linear transformations such as Gaussian, sigmoidal, or polynomial kernels, or fuzzy set memberships. At step 22, a similarity criterion is determined. In one embodiment, the similarity criterion may comprise similarity in the features that form the feature vector. For example, the similarity criterion may comprise a similarity, for example, in the biomarker expression levels, the area of individual cells or the compartments of the individual cells. In certain embodiments, in addition to the neighborhood features of the network theory, the methods and tools may comprise additional feature information such as morphology, texture, hardness, or combinations thereof.

At step 24, one or more classifiers may be used to select nodes that are qualified using the similarity criterion. A specific value may be assigned to the selected classifier depending on the tissue or gland type. Classifiers may provide information about the cell, as well as the tissue. For example, average betweenness may be used to reduce or eliminate the cluster connection between two glands (gland segmentation). An average betweenness may be defined as a ration of number of high betweenness cells over total number of cells. In embodiments where betweenness is selected as a classifier, a high betweenness may indicate that a cell is an import to the structure of a gland or is a link in connecting two glands into one cluster. A high betweenness may also denote a large cell, a cell in the center of the gland, or a cell without a neighboring cell on the rim of a gland.

When clustering coefficient is used as a classifier, cells with high clustering coefficients are regarded as tightly clustered, while the cells with lower values of lower values of the clustering coefficient are likely to be on the outside of a gland or cluster. The clustering coefficient is a measure of the transitivity of a node. A clustering coefficient of a tissue may be used as a differentiating feature of that tissue. When used as a classifier, the clustering coefficient may be used to separate certain glands from others. In one embodiment, a clustering coefficient of a node may be calculated by determining the number of connections that form transitive closures (node A to C where node A to B and B to C) over the number of possible $2^{nd}$ order connections.

At step 26, a first node from the BETN model is selected. The selection may be random or may be in a sequential order starting from one end of the image data and moving in a determined direction. At step 28, a second node is selected to be paired with the first cell. At step 30, a similarity criterion is applied to the pair of nodes.

In certain embodiments, the data to individual nodes, comprising information on the sub-cellular compartments (including membrane, cytoplasm and nucleus), may be stored in a database and the database is interrogated with network model to group nodes together on similarity criterion. The database may store information regarding the tissue and cells and the location in the subject from where the tissue is drawn. The location may include, for example, the particular cell from which a measurement is taken. The information may include a reference to the compartment of the cell (nucleus, membrane or cytoplasm) from where the measurements are drawn. In certain embodiments, the original measurement values and the location, cell or compartment of the cell, from which measurement is acquired/drawn may be stored, for example, in a database.

In certain embodiments, an overlay image may be produced with annotations corresponding to different tissue types. The annotations may be displayed as an overlay with a reference tissue image to provide easily-discernible tissue classification results, for example, indicating regions of concern for the purposes of biopsy, treatment, diagnosis, and/or further (follow-up) examination. The reference image may be a real-time or stored/captured colposcopic image, for example.

If the similarity criterion is satisfied, a link is formed in the BETN model between the first and second nodes (step 32). The BETN model may be updated to reflect the link formation between the nodes (step 34). In one embodiment, an annotation tool may be used to overlay colored dots from protein expressions corresponding to a particular biomarker above the original image. The annotation tool may be adapted to allow the user to select one or more types of cells from the images. For example, the annotation tools may allow the user to select stroma and epithelial cells.

If the similarity criterion is not satisfied, at step 36, another node, different from the second node, may be selected to form a pair of first node with the other node. Steps 30 to 34 are repeated. In addition, when the similarity criterion is not satisfied the BETN model may be updated to reflect the same.

Once the pairing of the first node is checked with the other nodes, a different node may be selected, and its pairing may be checked with the nodes of the network by following the steps 20-36.

Figure 3:
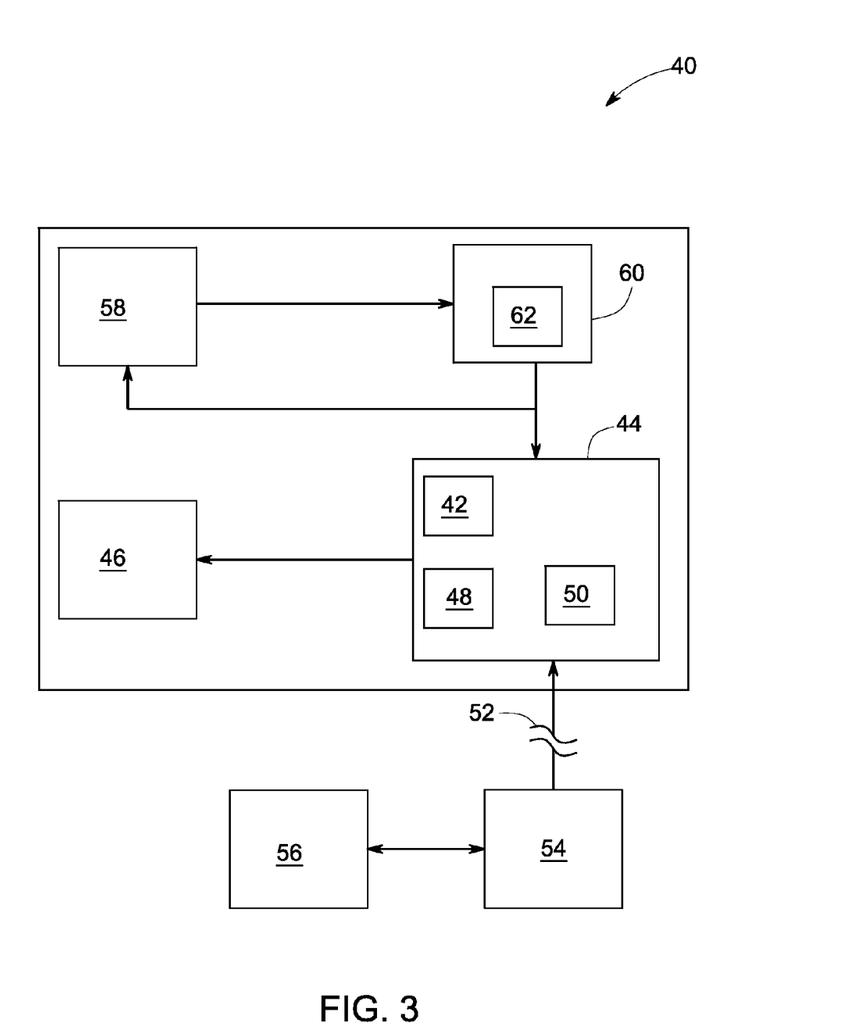
FIG. 3 is a block diagram of an example system for tissue classification using individual cells as nodes in a BETN of a tissue sample.

In certain embodiments, a system for enhanced tissue classification is provided. FIG. 3 illustrates a system 40 for carrying out the methods for enhanced tissue classification. The system 40 may be an automated system that requires least manual intervention for classifying the tissues in a given image. The image may comprise, but is not limited to, one or more structures selected from a group consisting of: cellular structures, vascular structures, and neural structures.

The system may comprise a storage device 42 for at least temporarily storing one or more images. The storage device may comprise, but is not necessarily limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the processor or the means for displaying the images, and yet still be accessed through any suitable connection device or communications network including but not limited to local area networks, cable networks, satellite networks, and the Internet, regardless whether hard wired or wireless.

The storage device may be a processor 44 that transforms the tissue image data into network data such that each node of the network corresponds to a cell in the tissue image data. The processor or CPU may comprise a microprocessor, microcontroller and a digital signal processor (DSP).

In one of the embodiments, the storage device 42 and processor 44 may be incorporated as components of an analytical device such as an automated high-throughput system that stains and images tissue micro arrays (TMAs) in one system and still further analyzes the images. The system 40 may further comprise a display device 46 to display one or more of the images; an interface 48; a microscope 50; and/or a transmitting device 52 one or more of the images or any related data or analytical information over a communications network 54 to one or more remote locations 56.

The display device 46 may comprise any suitable device capable of displaying a digital image such as, but not limited to, devices that incorporate an LCD or CRT. The transmitting device 52 may comprise any suitable transmitting device digital information over a communications network including but not limited to hardwired or wireless digital communications systems. The system 40 may further comprise an automated device 58 for applying one or more of the stains and a digital imaging device 60 such as, but not limited to, an imaging microscope comprising an excitation source 62 and capable of capturing digital images of the TMAs. Such imaging devices are preferably capable of auto focusing and then maintaining and tracking the focus feature as needed throughout processing.

In one embodiment, the interface 48 may be an interactive interface that allows visual inspection on different parameters, such as network characteristics. In another embodiment, the interface may allow a user to manually create links between the cells these links may be analyzed for similarity (e.g., like the annotation tool). In one example, the user may select a cell to cell relationship of interest, and the tool automatically creates additional links between the cells that share a similar relationship. In another embodiment, the user may modify an existing link function. The interactive interface may allow the link function to be updated in real time, so that the user may choose desirable stains or other information, and ways of calculating the information. In certain embodiments, such as in a touch screen, the display 46 and the user interface 48 may overlap. Also, in some embodiments, the display 46 and the user interface 48 may include a common area. For example, the display 46 may be a touch screen that may display the classification results, and may also accept inputs from the user. In one embodiment, the interface 48 may comprise a mouse-type device, a trackball, a joystick, a stylus, or a touch screen configured to facilitate the clinician to identify the one or more regions of interest requiring therapy. However, as will be appreciated, other human interface devices, such as, but not limited to, a touch screen, may also be employed. The interface 48 may be configured to aid the clinician in navigating through the images acquired by the medical imaging system 40.

Figure 4:
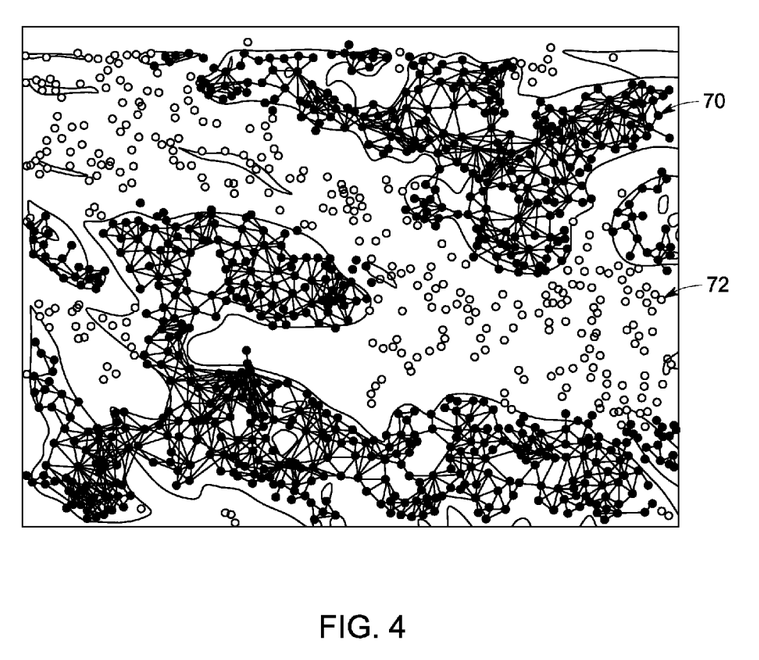
FIG. 4 is an image of an example BETN of a tissue sample after undergoing tissue classification to differentiate between two or more tissue types in the tissue sample.
Figure 5:
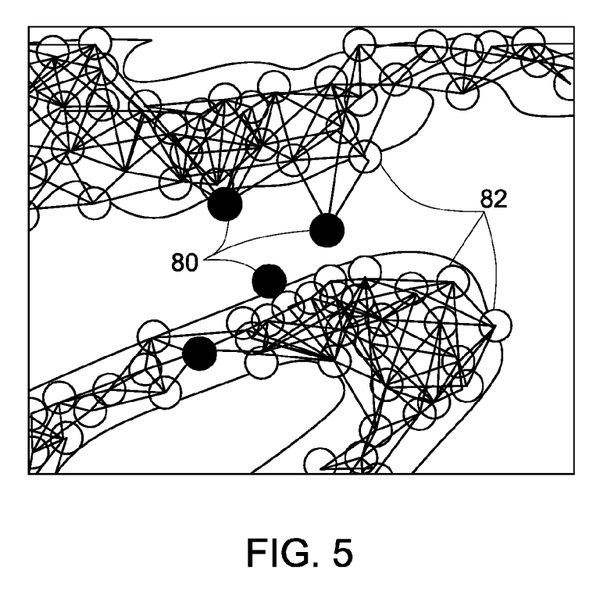
FIG. 5 is an image of a portion of an example BETN where connectivity algorithm comprises betweenness as a neighborhood based feature to classify the tissue

FIG. 4 is an image of a BETN, where the distance is modified by stain levels as a determinant of connectivity. The networks of epithelial cells, generally represented by solid circles 70, are connected to each other using a suitable threshold value. In the illustrated embodiment, the distance between the nodes represented by the hollow circles 72 in combination with the stain levels of the nodes 72 may be used as a determinant of connectivity. In one example, the network of the nodes 72 when set to the proper threshold value for the active network feature, such as the cluster size, may determine the connectivity. In the illustrated embodiment, the nodes 72 indicate that the active network feature, in this case cluster size, is above 5. That is, each node is directly or indirectly (via other nodes) connected to at least 5 nodes in the BETN. The nodes represented by the dotted circles 74 represent the cells that are not of interest, hence, the network attributes for these cells are not determined in the illustrated embodiment. However, in an alternate embodiment, these nodes 74 may be selected FIG. 5 illustrates an image of a BETN where connectivity algorithm comprises betweenness as a neighborhood based feature to classify the tissue. Betweenness represents the measure of how many shortest paths in a network use a given node. In the illustrated embodiment, the high betweenness values for the nodes 80 indicate that the cells are connecting to another gland represented by the nodes 82. The high betweenness value of the nodes 80 along with few like neighbors.

Figure 6:
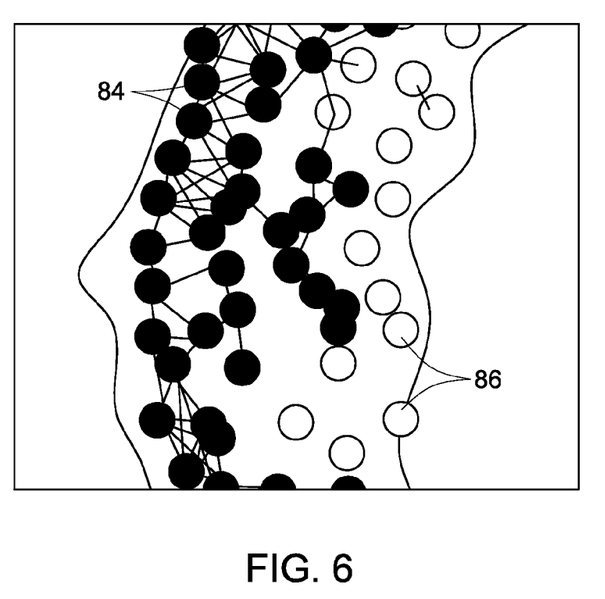
FIG. 6 is an image of a portion of an example BETN where connectivity algorithm comprises clustering coefficient as a neighborhood based feature to classify the tissue.

FIG. 6 illustrates an image of a BETN where a connectivity algorithm comprises a clustering coefficient as a neighborhood based feature to classify the tissue. In the illustrated embodiment, the clustering coefficient of the nodes 84 corresponding to selected cell types is measured. The clustering coefficients are indicated as numerical values against the corresponding nodes are a measure of transitivity in the network. In the illustrated embodiment, different areas of a gland, such as those on the outer edge, may have different clustering coefficients than ones in the center or elsewhere. Also, different gland and tissue types may have different clustering properties that may be used for differentiation of the cells. The clustering coefficient of the nodes 86 corresponding to different cell types is indicated as 0, as the connections between these cells may not be determined.

Figure 7:
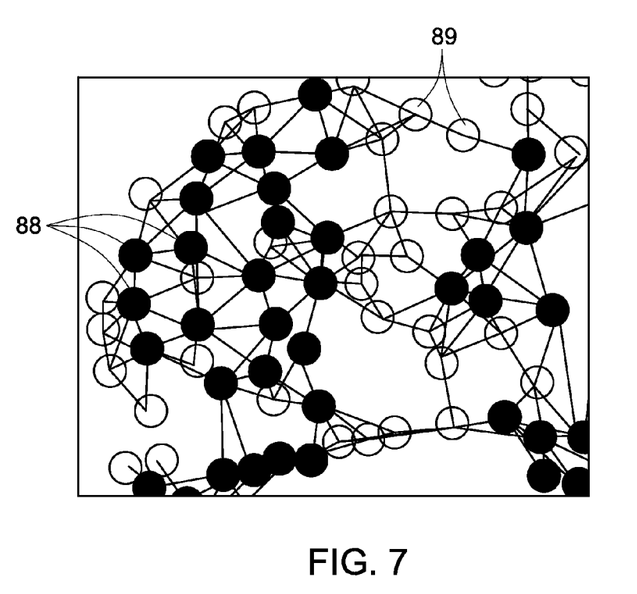
FIG. 7 is an image of an example BETN where connectivity algorithm comprises degrees as a neighborhood based feature to classify the tissue.

FIG. 7 illustrates an image of a BETN where connectivity algorithm comprises degrees as a neighborhood based feature to classify the tissue. In the illustrated embodiment, the degrees of the nodes 88 and 89 corresponding to particular cell types are individually depicted. The degrees of the nodes 88 and 89 are representative of direct connections that a node forms with other nodes. Like clustering coefficient, degree of a node provides an indication of the position of the node in the tissue. The position of the node is used to determine the position of the cell within the tissue. The degree of the node increases linearly as the threshold setting of the network increases. Thus, the degree or the clustering coefficient of the node may be used for determining the threshold settings.

Figure 8:
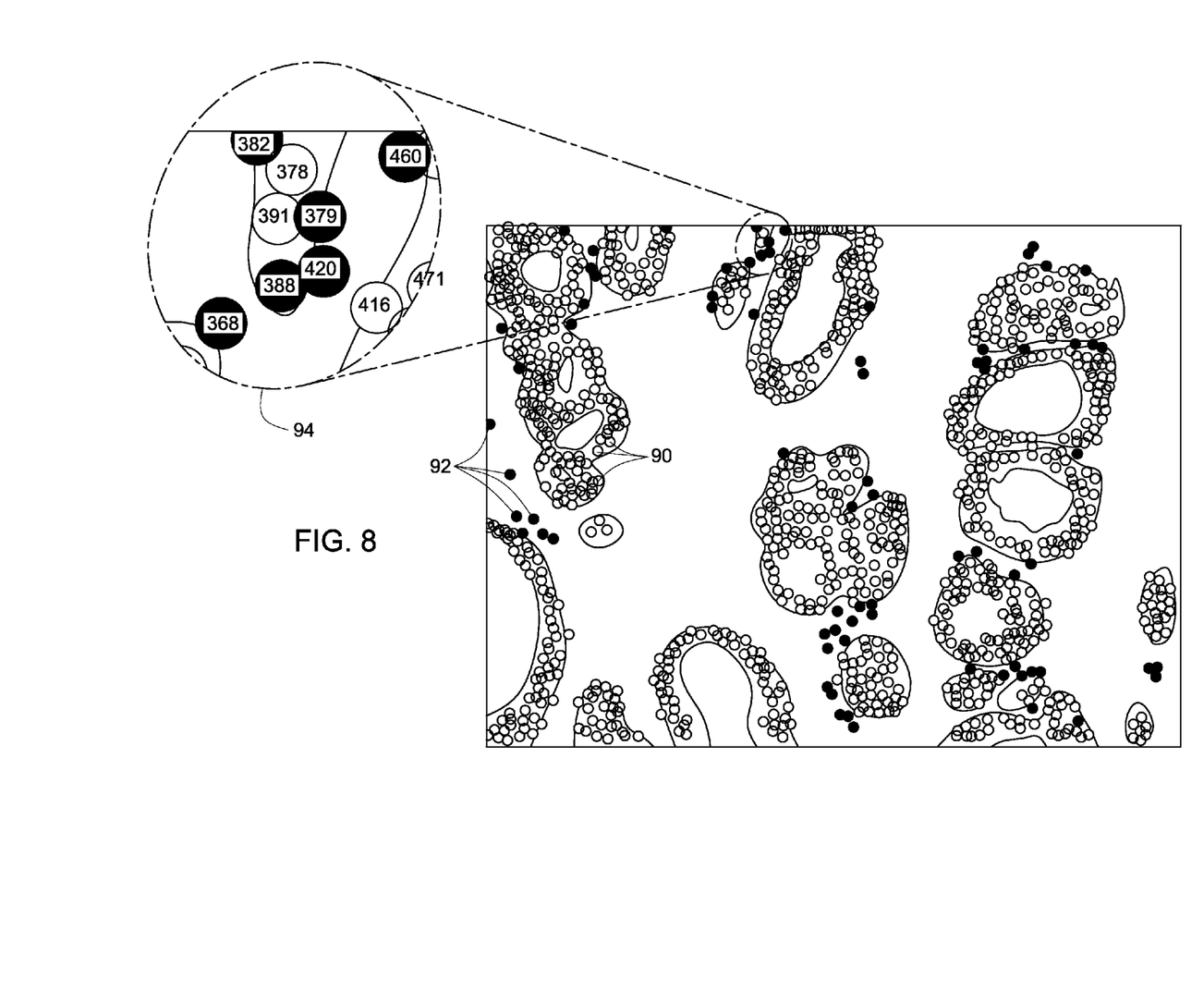
FIG. 8 is an image of an example of a biomarker stained tissue image data with individual cell identities overlaid on corresponding nodes.

FIG. 8 illustrates a biomarker stained tissue image data with individual cell identities (IDs) overlaid on corresponding nodes corresponding to cell types 90 and 92. As illustrated in an exploded view of a portion of the tissue image data, represented by reference numeral 94, overlaying the individual cell IDs translates the BETN into tissue image data by identifying the different nodes as individual cells. The groupings or segmentation of cells may be visualized by an overlay of the cell IDs on the nodes of the BETN. The overlay may show the distribution of different types of cells in the original tissue image. In one example, images from different tissue samples with such overlays may be compared to determine, for example, if the patterns of cells with one or more profiles, e.g., patterns of cells which belong to one or more groups, are indicative of any biological condition or process. For instance a clinical study could be undertaken to establish an association between a given pattern and a certain diagnosis or prognosis such as survival time for a certain type of cancer.

The groupings may also form a basis for investigating associations between a biological condition and a given cell attribute. Each grouping may be examined to identify any cell attribute which is associated with the diagnoses or prognoses of a given condition or disease or with the response to a given therapy for a given condition or disease. For instance, in a particular cell group it may be that the level of expression of a given biomarker is associated with a response to a given therapy, for example, administration of a drug, even though the level of expression for that biomarker in the tissue in general does not display such an association.

EXAMPLE

An algorithm was performed for feature selection. Using the 18 features listed below, with the addition of preliminary clustering features as genes, chromosomes of features were mutated, crossed over, and then selected using an SVM as a fitness function. Mutation and crossover was performed by taking two parent chromosomes (paired at random), keeping their common genes, then selecting a gene from the first parent only with a 40% chance, from the second parent only, another 40% chance, and a 20% chance of a random gene mutation (neither parent). Also, there was a small chance of dropping any gene at random, including a common one, to prevent premature convergence. The child chromosome size would be within a range created by the difference of the two parents' sizes added or subtracted to the parent with the higher fitness. The results shows that the clustering at threshold 40 and area of the cell tied with the most appearance in the final round, with area of the nucleus, mean cytoplasm keratin level, minimum membrane keratin level, and the proximity values of 30 and 20 all scoring highly.

TABLE 1

Feature Vector for SVM Experiments

| Feature Name | Feature Description |
| --- | --- |
| Area_Cell | Area of the Cell |
| Area_Nuc | Area of the Nucleus |
| Area_Memb | Area of the Membrane |
| Area_Cyt | Area of the Cytoplasm |
| Mean-Memb-Keratin | Mean Keratin Level of Membrane |
| Std-Memb-Keratin | Std Deviation Keratin Level of Membrane |
| Max-Memb-Keratin | Maximum Keratin Level of Membrane |
| Min-Memb-Keratin | Minimum Keratin Level of Membrane |
| Mean-Cyt-Keratin | Mean Keratin Level of Cytoplasm |
| Std-Cyt-Keratin | Std Deviation Keratin Level of Cytoplasm |
| Max-Cyt-Keratin | Maximum Keratin Level of Cytoplasm |
| Min-Cyt-Keratin | Minimum Keratin Level of Cytoplasm |
| Within-5 | Number of other Cells within 5 pixels |
| Within-10 | Number of other Cells within 10 pixels |
| Within-15 | Number of other Cells within 15 pixels |
| Within-20 | Number of other Cells within 20 pixels |
| Within-25 | Number of other Cells within 25 pixels |
| Within-30 | Number of other Cells within 30 pixels |

A keratin stained BETN was developed using 12 keratin features and was used to perform epithelial classification on multiple patients with multiple tissue types. This required no other features beyond cluster size, which is the measure of how many other cells to which a cell is directly and indirectly connected. This basic feature was found to be almost linearly correlated with an epithelial cell. Furthermore, if the tissue sample comprises multiple, distinct glands, the clusters are often gland specific and may be used to segment and compare glands.

The availability of a database is useful for iterative and interactive investigations, for example, of how biomarker groupings change in the context of various biological questions. For example, all cells that are positive for Glut1, indicative of hypoxia, may be highlighted and expression of biomarkers associated with those positive cells may be visualized. This is particularly useful for quality control assessments and investigations of new hypotheses.

The groupings may also be conveniently used to guide a numerical analysis to identify one or more biomarkers whose levels of expression in a given group of cells is indicative of the presence, prognoses or response to treatment of a condition or disease. The biomarker expression level data was available for cells from tissue of one or more control subjects and from tissue of one or more subjects with the condition or disease or subjected to a treatment of interest. This data was then examined to identify associations in the level of expression of any biomarker in any given group between cells from the control subjects and cells from the target group.

One or more of the method steps may be performed by a suitably programmed computer. A suitable computer may be implemented, for example, using computer processors, memory units, storage devices, computer software, and other components. In certain embodiments, the processor may be configured to control the operation of the computer by executing computer program instructions which define such operation. The computer program instructions may be stored in a storage device (e.g., magnetic disk, optical disk, or any other computer readable medium) and loaded into memory when execution of the computer program instructions is desired. The memory may be used to store data used during the various steps of the method. The computer may also comprise one or more interfaces for communicating with other devices (e.g., locally or via a network). The computer may also comprise input/output devices that allow for user interaction with the computer (e.g., display, keyboard, mouse, speakers, buttons, etc.). In some embodiments, the processing steps described herein may also be implemented using dedicated hardware. The circuitry of the hardware may be configured for implementing such processing steps. Alternatively, the processing steps may be implemented using various combinations of hardware and software. Further, in various implementations, the functions described herein may be performed on a dedicated apparatus, or the functions may be part of a device that performs other functions as well.

The methods for characterizing and quantifying biomarker protein expressions in the tissue images of interest may be used for, but are not limited to, diagnosis, prognosis, drug discovery, and specific biological knowledge discovery. The methods for tissue classification may be applied, for example, to any tissue that is likely to vary in some manner as a result of its biological condition or history. For instance, the methods may be applied, for example, for a diagnosis of a condition by obtaining appropriate tissue samples from subjects with and without a particular condition or disease. Alternatively, the methods may be applied for a prognosis of a disease or condition using appropriate historical tissue from subjects whose later clinical outcomes were known. Thus, the methods may be applied to improve the prediction of survival rates in colon cancer patients from that available from the ratio of cMET expression in cytoplasm to that in membrane in which the ratio is based upon all the cells in the examined tissue. The methods may be applied to assess the effects of various treatments on a disease or condition. For example, the methods may be used to compare tumor tissue from untreated model animals to tumor tissue from model animals treated with one or more drugs.

The systems and methods provide improved treatments, especially targeted and patient specific therapies, while reducing costs and human errors in medicine and medical research. The systems and methods may also report the nature of different tissues, aggregate cell interactions, and the relationship between protein expression and tissue formation.

Advantageously, the methods may be used to show invariance with respect to tissue types. The network design does not require, for example, labeled training data. Further, the network data comprises adjustable sensitivity tuning. In certain embodiments, the methods do not require any training, may adjust sensitivity depending on an application, and may be configured in an infinite number of ways to provide infinite features for differentiating tissue and discovering knowledge.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method for tissue classification of a tissue sample, comprising:
    acquiring tissue image data for the tissue sample;
    transforming the tissue image data to a biomarker enhanced tissue network (BETN) such that an individual cell or a sub-cellular structure in the tissue image data corresponds to a node in the BETN;
    defining a feature vector based on a feature set representative of a tissue type, wherein the feature set comprises one or more attributes of the BETN and one or more features of tissues and cells in the tissue sample;
    determining a similarity criterion for one or more features of the feature set based on the feature vector;
    grouping nodes of the BETN based on the similarity criterion; and
    classifying the nodes in the tissue image data based on the grouping of the nodes of the BETN.

2. The method of claim 1, wherein the tissue image data comprises spatial information, morphological information, biomarker information, or combinations thereof.

3. The method of claim 1, further comprising determining a feature set, wherein determining the feature set comprises:
    determining a plurality of features of the tissues and the cells in the tissue sample, wherein the plurality of features comprise cell features, sub-cellular features, protein expression based features, or combinations thereof; and
    selecting one or more features from the plurality of features that are representative of a target of interest.

4. The method of claim 1, wherein classifying the nodes comprises using an algorithm to determine connectivity between a pair of nodes in the BETN.

5. The method of claim 4, wherein the algorithm uses neighborhood based features, or classifier algorithms for determining frequent subgraphs.

6. The method of claim 4, wherein the neighborhood based features comprise robustness, betweenness, cluster size, clustering coefficient, degrees, centrality, flow, or combinations thereof.

7. The method of claim 4, wherein the algorithm is at least in part derived using one or more of Center-Piece Subgraphs (CePS), Graph-based Hierarchical Conceptual Clustering, SUBstructure Discovery Using Examples (SUBDUE), Apriori-based Algorithm, GrAph, Sequences, and Tree extraction (GASTON), Graph-based induction, SPanning tree based maximal graph mINing (SPIN), Graph-based Substructure Pattern Mining (gSpan), Fast Frequent Subgraph Mining (FFSM), Leap Search, or combinations thereof.

8. The method of claim 5, wherein the neighborhood based features are derived or classification is performed by converting graphs into trees or forming trees directly from the tissue image data.

9. The method of claim 1, further comprising pre-processing the tissue image data to define the feature vector.

10. The method of claim 9, wherein pre-processing the tissue image data comprises providing baseline results prior to grouping the nodes.

11. The method of claim 10, wherein providing the baseline results comprises applying supervised machine learning for the feature vector.

12. The method of claim 10, further comprising revising the feature set based on the baseline results.

13. The method of claim 12, further comprising determining a baseline mean of the tissue sample for one or more features of the revised feature set.

14. The method of claim 13, further comprising comparing an average value of a feature of the revised feature set for a pair of nodes to the baseline mean to determine a possibility of a connection between the nodes of the pair of nodes.

15. The method of claim 1, wherein the grouping of the nodes comprises analyzing data representative of the BETN, original spatial data, protein expression data, or combinations thereof.

16. The method of claim 1, further comprising updating the BETN when a link is formed between a pair of nodes.

17. The method of claim 1, further comprising identifying one or more misclassified nodes in the tissue sample.

18. The method of claim 1, further comprising:
    manually identifying a cell or a cell to cell relationship in the BETN; and
    forming a training model based on the identified cell or the cell to cell relationship to identify similar cells or relationships in the BETN.

19. The method of claim 1, further comprising overlaying a set of protein expression data for cells of the tissue sample onto the tissue image data.

20. The method of claim 19, further comprising mapping classification data of the nodes on corresponding cells of the tissue image data.

21. The method of claim 1, wherein acquiring the tissue image data comprises acquiring two or more tissue images of a field of view of a microscope for a tissue sample treated to reveal protein expression data for one or more biomarkers.

22. The method of claim 1, further comprising determining the BETN, wherein determining the BETN comprises:
    determining a probabilistic network; and
    combining a set of protein expression data corresponding to one or more biomarkers for each node of the probabilistic network to determine the BETN.

23. A method for tissue classification of a tissue sample, wherein the tissue sample has been treated to reveal one or more levels of protein expression of one or more biomarkers, the method comprising:
    acquiring one or more tissue images of a tissue sample;
    determining a probabilistic network based on the one or more tissue images such that each node in the probabilistic network corresponds to a cell in the one or more tissue images;
    determining a biomarker enhanced tissue network (BETN) by combining the one or more levels of protein expression of the one or more biomarkers;
    determining a feature vector based on a feature set of the BETN whereby the feature vector is representative of a tissue type of interest, wherein the feature set comprises one or more attributes of the BETN and one or more features of tissues and cells in the tissue sample;
    determining a similarity criterion for one or more features of the feature set based on the feature vector;
    determining nodes that satisfy the similarity criterion based on the feature vector;
    classifying the nodes using an algorithm; and
    overlaying classification data of the nodes on corresponding cells of the tissue images.

24. An image analysis system for analyzing a tissue sample, comprising:
   an imaging device configured to image the tissue sample; and
   a processor programmed to determine a biomarker enhanced tissue network (BETN) based on tissue image data whereby an individual cell in the tissue image data corresponds to a node in the BETN, define a feature vector based on a feature set representative of a tissue type of interest, determine a similarity criterion for one or more features of the feature set based on the feature vector, cluster nodes of the BETN based on the similarity criterion of the feature set of the nodes, and classify cells in the tissue image data based on the grouping of nodes of the BETN, wherein the feature set comprises one or more attributes of the BETN and one or more features of tissues and cells in the tissue sample.

25. The system of claim 24, further comprising an interactive interface configured to manually group two or more cells of the tissue sample.

* * * * *